US00PP22015P2

(12) United States Plant Patent
Probst

(10) Patent No.: US PP22,015 P2
(45) Date of Patent: Jul. 5, 2011

(54) ***COREOPSIS* PLANT NAMED 'JIVE'**

(50) Latin Name: ***Coreopsis* hybrid**
Varietal Denomination: Jive

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/660,491

(22) Filed: Feb. 26, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Kent L Bell
(74) *Attorney, Agent, or Firm* — Penny J. Aguirre

(57) ABSTRACT

A new cultivar of hybrid *Coreopsis* named 'Jive' characterized by its inflorescences with ray florets that are white in color with a large burgundy-purple eye zone, its bushy and relatively short plant habit, its floriferous and long blooming habit, its relative sterility, and its vigorous growth habit.

2 Drawing Sheets

Botanical classification: *Coreopsis* hybrid.
Variety denomination: 'Jive'.

CROSS REFERENCE TO A RELATED APPLICATION

This application is co-pending with a U.S. Plant Patent application filed for a plant derived from similar parentage in the Inventor's breeding program that is entitled *Coreopsis* Plant Named 'Caliente' (U.S. patent application Ser. No. 12/661,060), *Coreopsis* Plant Named 'Salsa' (U.S. patent application Ser. No. 12/660,464), *Coreopsis* Plant Named 'Limbo' (U.S. patent application Ser. No. 12/660,455), *Coreopsis* Plant Named 'Mambo' (U.S. patent application Ser. No. 12/660,454), *Coreopsis* Plant Named 'Cha Cha Cha' (U.S. patent application Ser. No. 12/660,480).

BACKGROUND OF THE INVENTION

The present invention relates to a new and distinct cultivar of *Coreopsis* plant, botanically of hybrid origin and known as *Coreopsis* 'Jive' and will be referred to hereinafter by its cultivar name, 'Jive'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique inflorescence colorations, short and bushy plant habits, and sterility to lengthen bloom periods.

The Inventor made a controlled cross in August 2006 in his test garden in Hubbardston, Mass. between an unnamed F6 generation seedling produced with crosses of *Coreopsis tinctoria* and *Coreopsis rosea* as the female parent and an unnamed F6 generation seedling produced with crosses of unnamed hybrid *Coreopsis* from his breeding program and

*Coreopsis rosea* as the male parent. 'Jive' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Jive' as unique from all *Coreopsis* cultivars known to the Inventor.

1. 'Jive' exhibits composite inflorescences with ray florets that are white in color with a large dark burgundy-purple eye zone.
2. 'Jive' exhibits a bushy plant habit and is relatively short in height; reaching 12 to 18 inches (30 to 45 cm) in height.
3. 'Jive' exhibits a vigorous growth habit.
4. 'Jive' exhibits a long blooming period with an abundance of blooms; blooming from June through August in Massachusetts.
5. 'Jive' is relatively sterile and produces very few seeds if any.

The female parent differs from 'Jive' in having a shorter plant height (reaching 8 to 12 inches in height), in having inflorescences with ray florets that are white in color with a small burgundy eye, and in producing an abundance of seed that shortens its bloom season to one month. The male parent differs from 'Jive' in being taller in plant height (reaching 18 to 24 inches in height), in being less floriferous and in having inflorescences with ray florets that are solid gold in color. 'Jive' can be most closely compared to cultivars from the same parentage, 'Mambo' and 'Salsa'. They are both similar to 'Jive' blooming habit. 'Mambo' differs from 'Jive' in having inflorescences with ray florets that open creamy white in color with a smaller burgundy eye zone. 'Mambo' also differs in that the white portion of the ray floret ages in a few days to a rose-purple color. 'Salsa' is similar to 'Jive' in having inflorescences with ray florets with a large red eye zone, however 'Salsa' differs from 'Jive' in having ray florets that are gold in color.

BRIEF DESCRIPTION OF THE DRAWING

The accompanying colored photographs illustrate the overall appearance and distinct characteristics of the new *Coreopsis*. The photographs in the figures were taken in late summer of a five month-old plant of 'Jive' as grown outdoors in a large mixed container planting in New Hope, Minn.

The photograph in FIG. 1 shows the floriferous blooming habit of 'Jive'.

Figure 1:
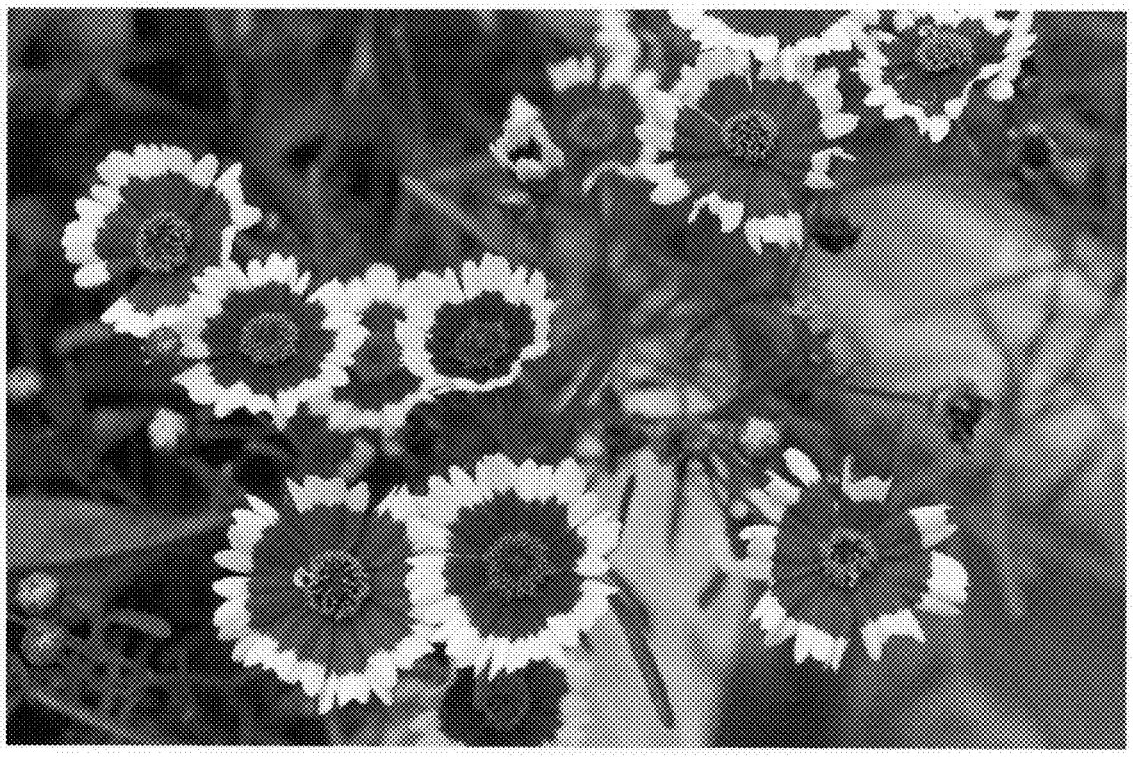
Figure 2:
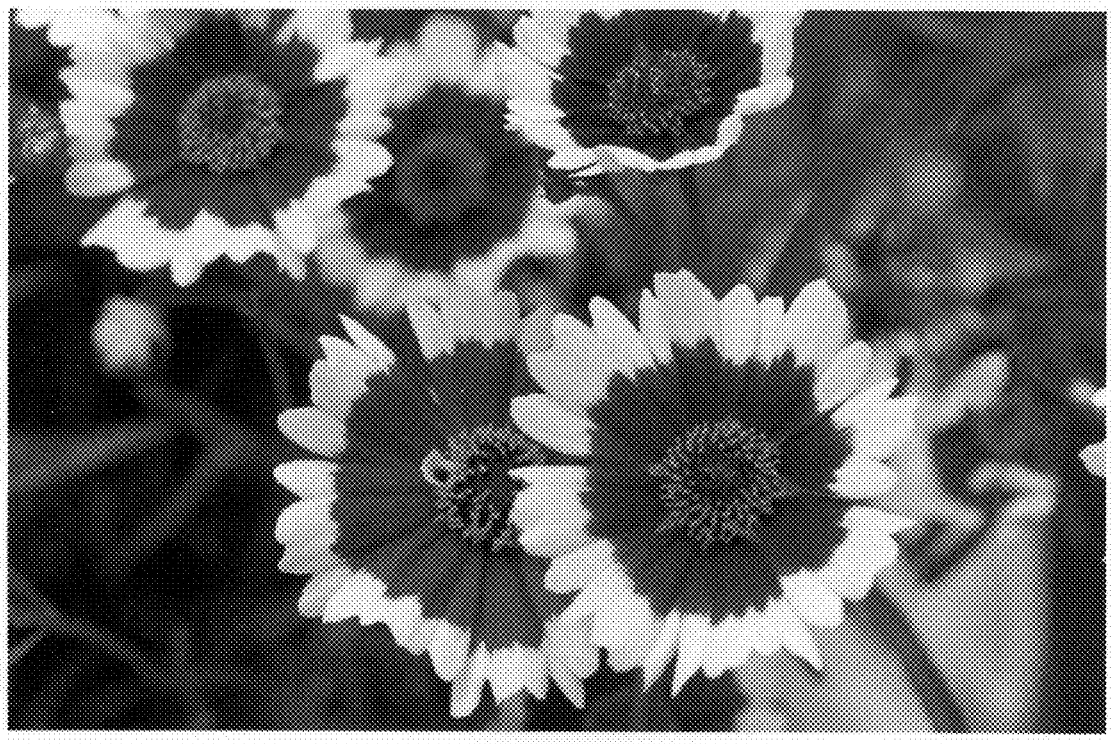

The photograph in FIG. 2 provides a close-up view of inflorescences of 'Jive'. The Colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms from June through August in central Massachusetts.

*Plant habit.*—Herbaceous annual, well-branched to produce a bushy habit.

*Height and spread.*—Reaches 12 to 18 inches (30 to 45 cm) in height and 12 to 15 inches (30 to 38 cm in width) in 3 months from a rooted cutting.

*Cold hardiness.*—Has not been tested as it is grown as an annual.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous.

Stem description:

*Shape.*—Oval, solid.

*Stem color.*—144A.

*Stem size.*—Main stem averages 18 cm in length and 3 mm in width with laterals variable in length with an average of 8 cm in length (excluding peduncles) and 1.5 mm in width.

*Stem surface.*—Very finely puberulent when young, ridged and puberulent when mature.

*Branching habit.*—Numerous basal branches (an average of 15 per one year-old plant) with an average of 4 secondary branches opposite at a nodes; first pair commencing about 12 cm from the base with second pair at about 16 cm from base.

Foliage description:

*Leaf division.*—Simple.

*Leaf margins.*—Entire with slight undulations.

*Leaf size.*—Variable, an average of 7 cm in length and width when mature with center lobe an average of 7 mm in length and 5 mm in width and secondary lobes an average of 3 cm in length and 4 mm in width.

*Leaf shape.*—Very narrowly oblanceolate.

*Leaf base.*—Attenuate.

*Leaf apex.*—Broadly acute.

*Leaf venation.*—Pinnate, not conspicuous, coloration same as leaf on both surfaces.

*Leaf attachment.*—Sessile.

*Leaf arrangement.*—Opposite.

*Leaf surface.*—Dull and very finely puberulent on upper surface and lower surface.

*Leaf color.*—Young and mature upper surface; 137A, young and mature lower surface; 137B.

Flower description:

*Inflorescence type.*—Composite with ray florets surrounding disk florets in the center, forming a radiant head, inflorescences are borne on terminals of lateral branches on thin peduncles.

*Lastingness of inflorescence.*—About one week until senescence of ray florets, bracts and disk florets are persistent.

*Fragrance.*—None detected.

*Quantity of inflorescences.*—An average of 8 per lateral branch, an average of 100 per plant grown in a one-gallon container.

*Inflorescence size.*—Up to 1 cm in depth and up to 2.5 cm in diameter with disk portion up to 7 mm in diameter.

*Inflorescence buds.*—Average of 5 mm in depth and 6 mm in diameter, shape is spherical but flattened, color when first formed is 176A becoming 150B surrounded with bracts that are 26A in color at apex blending to 147A at base.

*Peduncle.*—Strong, thin, average of 7.5 cm in length and 1 mm in diameter, a blend of 144A and 146A in color, surface is glabrous with fine ridges.

*Pedicels.*—None.

Involucral bracts:

*Bract number.*—Two rows of 5 outer bracts, and two rows of 4 inner bracts.

*Bract arrangement.*—Outer bracts are fused into cone-shaped base about 2 mm in length and width with free apex of each held slightly upward, inner bracts overlap and surround receptacle with a campanulate form with apical portion un-fused, spreading, and held close to ray florets.

*Bract size.*—Outer bracts; up to 7 mm in length and 1.5mm in length with free portion an average of 3 mm in length and 1.5 mm in width, inner bracts; up to 7 mm in length and 3 mm in width with free portion an average of 4 mm in length and 3 mm in width.

*Bract color.*—Outer bracts; 137B on both surfaces with thin margins 144A and tip of apex 176A, inner bracts; fused portion 147A, un-fused portion 26A.

*Bract texture.*—Waxy on outer and inner bracts.

*Bract apex.*—Acute on outer and inner bracts.

*Bract base.*—Truncate on outer and inner bracts.

*Bract margins.*—Entire with fine short hairs on outer bracts.

*Bract shape.*—Outer bracts; free portion ovate, inner bracts; free portion broadly lanceolate.

Ray florets (sterile):

*Number.*—8.

*Shape.*—Obovate, appearance of three longitudinal sections with center section slightly longer and apex of each free.

*Size.*—An average of 1 cm in length and 8 mm in width.

*Apex.*—3-lobed with center lobe slightly emarginate and side lobes rounded.

*Base.*—Broadly cuneate.

*Margins.*—Entire on sides, lobed at apex.

*Aspect.*—Held slightly cupped upward when fully open.

*Texture.*—Glabrous on upper and lower surfaces with eye zone of upper surface velvety.

*Color.*—Upper surface when opening; 2C with eye zone (lower one-half of petal) 187A, lower surface when opening; 2C with eye zone suffused with N186B, upper surface when full open; NN155A with eye zone 187B, lower surface when fully open; 155B with eye zone suffused with N186C.

Disk florets (perfect):

*Shape.*—Tubular, corolla is fused, flared at apex.

*Size.*—About 6 mm in length and 1 mm in width.

*Color.*—In masse; 187A when immature, 166A and N25A when fully open and becoming a blend of 200A when dried and ray florets drop, corolla; base (tube) is 163C in color, flared portion is 187B and translucent.

*Number.*—Numerous, about 120.

*Receptacle.*—About 3.5 mm in diameter and 2 mm in depth, 1D in color.

Reproductive organs:

*Presence.*—Disk florets are perfect, ray florets are sterile.

*Gynoecium.*—1 Pistil, 5 mm in length, style is very fine and about 19C in color and translucent, bifid pilose stigma is N25A in color with branches about 0.7 mm in length and strongly recurved, ovary is oblong in shape, 2 mm in length, 0.7 mm in width, inferior, and 145D in color.

*Androecium.*—5 stamens, fused into tube surrounding style, 1 mm in length and 0.5 mm in width, about 200A in color, pollen moderate in quantity and 15A in color.

*Fruit/seed.*—Relatively sterile and produces very few seeds if any.

It is claimed:

1. A new and distinct cultivar of *Coreopsis* plant named 'Jive' as herein illustrated and described.

* * * * *